(12) United States Patent
John

(10) Patent No.: US 11,389,451 B2
(45) Date of Patent: Jul. 19, 2022

(54) METOLAZONE EMULSION FORMULATION

(71) Applicant: ACADEMIC PHARMACEUTICALS, INC., Lake Bluff, IL (US)

(72) Inventor: Somberg John, Lake Bluff, IL (US)

(73) Assignee: HYLORIS DEVELOPMENTS S.A., Liège (BE)

( * ) Notice: Subject to any disclaimer, the term of this patent is extended or adjusted under 35 U.S.C. 154(b) by 51 days.

(21) Appl. No.: 16/640,964

(22) PCT Filed: Sep. 11, 2018

(86) PCT No.: PCT/US2018/050340
§ 371 (c)(1),
(2) Date: Feb. 21, 2020

(87) PCT Pub. No.: WO2019/055370
PCT Pub. Date: Mar. 21, 2019

(65) Prior Publication Data
US 2020/0179386 A1 Jun. 11, 2020

Related U.S. Application Data

(60) Provisional application No. 62/557,210, filed on Sep. 12, 2017.

(51) Int. Cl.
| | | |
|---|---|---|
| *A61K 31/517* | (2006.01) |
| *A61K 9/107* | (2006.01) |
| *A61K 47/10* | (2017.01) |
| *A61K 47/18* | (2017.01) |
| *A61K 47/22* | (2006.01) |
| *A61K 47/24* | (2006.01) |
| *A61K 47/34* | (2017.01) |
| *A61K 47/44* | (2017.01) |
| *A61K 51/04* | (2006.01) |

(52) U.S. Cl.
CPC ............ *A61K 31/517* (2013.01); *A61K 9/107* (2013.01); *A61K 47/10* (2013.01); *A61K 47/183* (2013.01); *A61K 47/22* (2013.01); *A61K 47/24* (2013.01); *A61K 47/34* (2013.01); *A61K 47/44* (2013.01); *A61K 51/0419* (2013.01)

(58) Field of Classification Search
CPC ...... A61K 31/517; A61K 9/107; A61K 47/10; A61K 47/183; A61K 47/22; A61K 47/24; A61K 47/34; A61K 47/44; A61K 51/0419
See application file for complete search history.

(56) References Cited

U.S. PATENT DOCUMENTS

| | | | |
|---|---|---|---|
| 4,784,845 A * | 11/1988 | Desai ................... | A61K 9/107 514/216 |
| 4,801,455 A | 1/1989 | List et al. | |
| 6,048,874 A | 4/2000 | Santelli et al. | |
| 7,595,348 B2 | 9/2009 | Chattopadhyay et al. | |
| 8,241,664 B2 | 8/2012 | Dudley et al. | |
| 8,414,914 B2 * | 4/2013 | Bromley ................ | A61K 9/006 424/450 |
| 8,546,453 B2 | 10/2013 | Zhang | |
| 8,658,676 B2 | 2/2014 | Motheram et al. | |
| 2007/0026024 A1 | 2/2007 | Drees | |
| 2010/0092526 A1 * | 4/2010 | Baker, Jr. ............ | A61K 31/047 424/400 |
| 2017/0258917 A1 | 9/2017 | Subbiah et al. | |
| 2018/0078566 A1 | 3/2018 | Dudley et al. | |

FOREIGN PATENT DOCUMENTS

| | | | |
|---|---|---|---|
| EP | 0215313 | * | 3/1987 |
| JP | 404069331 A | | 3/1992 |
| WO | 2009/006311 A2 | | 1/2009 |

OTHER PUBLICATIONS

PCT/US2018/0530340 Written Opinion of the International Searching Authority, dated Nov. 14, 2018.
JP 404069331 English Translation from the European Patent Office.
EP 18 85 6454 Extended European Search Report dated Apr. 1, 2021 (corresponding EP patent application).

* cited by examiner

*Primary Examiner* — Shirley V Gembeh
(74) *Attorney, Agent, or Firm* — Vance Intellectual Property, PC

(57) ABSTRACT

The present invention relates to pharmaceutical formulations comprising metolazone, a lipid, and an emulsifier that provide a lipid formulation of metolazone that can be administered intravenously to patients, thereby enhancing the therapeutic delivery and improving patient care for acute heart failure and resistant edmitious states.

19 Claims, 1 Drawing Sheet

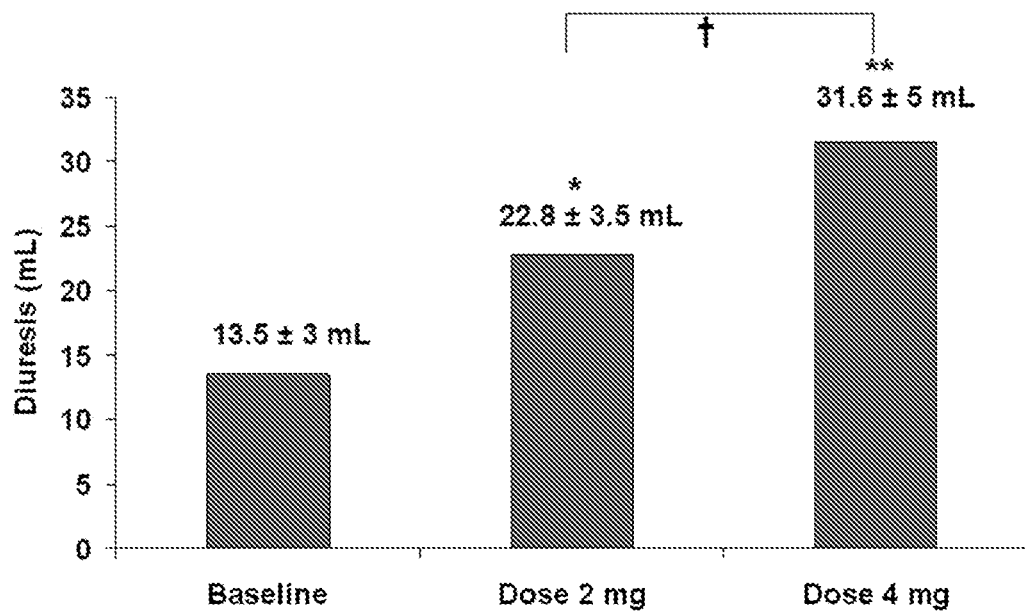

METOLAZONE EMULSION FORMULATION

FIELD OF THE INVENTION

The present invention relates to stable metolazone oil-in-water emulsion formulations.

BACKGROUND OF THE INVENTION

Metolazone is a thiazide-like diuretic that acts on the proximal as well as distal tubule of the kidney. It is characterized as a long-acting, highly effective diuretic that is typically used in a hospital setting as treatment for edematous states not responding to loop diuretics. The diuretic is uniquely effective in diuretic resistant states requiring hospitalization and aggressive implementation of diuretic therapy.

Metolazone is further characterized by having low solubility in water and moderate to high solubility in lipids. When metolazone is dissolved in oil-in-water emulsions, it results in better solubility and/or less side effects than when other formulations are utilized. The drug is approved for oral administration in the United States for the treatment of edematous states caused by heart, liver, or hepatic failure.

Lipid emulsion formulation can support microbial growth since it contains soybean oil and egg yolk phospholipids. Therefore, metolazone oil-in-water emulsion formulations require strict aseptic techniques during handling and administration to avoid microbial contamination that can cause infections among patients. To minimize the possibility of microbial contamination, it is recommended that such formulations be discarded four hours after opening. Such a requirement places a burden on health care providers in that fresh vials of the drug may be needed to continually obtain and set up while the patient is being treated.

Accordingly; there exists a need for a stable metolazone emulsion formulation that optionally possess anti-microbial properties, thereby providing greater ease in handling. Such a formulation would also result in cost savings to the health care providers and patients in decreasing the waste of metolazone.

SUMMARY OF THE INVENTION

In an aspect, the present invention provides a novel oil-in-water formulation, comprising: metolazone or a pharmaceutically acceptable salt thereof, a lipid, and an emulsifier.

In an aspect, the present invention provides a novel oil-in-water formulation, comprising: metolazone or a pharmaceutically acceptable salt thereof, an antimicrobial agent, a lipid, and an emulsifier.

In another aspect, the present invention provides a novel oil-in-water formulation, comprising: metolazone or a pharmaceutically acceptable salt thereof, an antimicrobial agent, a lipid, an emulsifier, and a co-emulsifier.

In another aspect, the present invention provides a novel oil-in-water formulation, comprising: metolazone or a pharmaceutically acceptable salt thereof, an antimicrobial agent, a lipid, an emulsifier, a co-emulsifier, and an antioxidant.

These and other objects, which will become apparent during the following detailed description, have been achieved by the inventor's discovery of the presently claimed formulations.

BRIEF DESCRIPTION OF THE DRAWINGS

FIG. 1 shows effect of two doses of methadone formulated according to the present invention.

DETAILED DESCRIPTION OF THE INVENTION

It is to be understood that the descriptions of the present invention have been simplified to illustrate elements that are relevant for a clear understanding of the present invention, while eliminating, for the purpose of clarity, many other elements found in typical pharmaceutical compositions and methods of stabilization. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the aspects identified herein are for exemplary purposes only, and are not meant to be exclusive or limited in their description of the present invention.

The formulations of the present invention are pharmaceutical formulations, i.e., formulations suitable for administration to a patient. Formulation and pharmaceutical formulation are used interchangeably.

In an aspect, the present invention provides a novel oil-in-water formulation, comprising: metolazone or a pharmaceutically acceptable salt, a lipid, and an emulsifier.

In another aspect, the present invention provides a novel oil-in-water formulation, comprising: metolazone or a pharmaceutically acceptable salt, an antimicrobial agent, a lipid, and an emulsifier.

In another aspect, the present invention provides a novel oil-in-water formulation, comprising: metolazone or a pharmaceutically acceptable salt, an antimicrobial agent, a lipid, an emulsifier, and a co-emulsifier.

In another aspect, the present invention provides a novel oil-in-water formulation, comprising: metolazone or a pharmaceutically acceptable salt, an antimicrobial agent, a lipid, an emulsifier, a co-emulsifier, and an antioxidant.

In another aspect, the present invention provides a novel metolazone oil-in-water emulsion formulation wherein metolazone is dispersed or dissolved in a lipid (e.g., soy bean oil), an emulsifier (e.g., L-α-lecithin, soybean (or other sources)), water, and optionally (e.g., to further stabilize) a co-emulsifier (e.g., a surfactant such as polysorbate 80). The tonicity of emulsion can adjusted with a tonicity agent (e.g., with glycerin). Optionally, the emulsion, further comprises: an amount of an antimicrobial (e.g., EDTA) sufficient to inhibit growth of microorganisms in the formulation in the event of accidental extrinsic contamination.

In another aspect, the present invention provides a novel metolazone oil-in-water emulsion formulation, comprising: metolazone, a lipid, an emulsifier, a tonicity modifier, an antimicrobial agent, and water.

In another aspect, the present invention provides a novel metolazone oil-in-water emulsion formulation, comprising: metolazone, a lipid, an emulsifier, a co-emulsifier, a tonicity modifier, an antimicrobial agent, and water.

In another aspect, the formulation, comprises: from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, to 10 mg/mL of metolazone or a pharmaceutically acceptable salt thereof. Additional examples include: from 0.2-2 mg/mL and from 0.5-1 mg/mL.

In another aspect, the formulation, comprises: an antimicrobial agent in an amount sufficient to inhibit growth of microorganisms in the formulation in the event of accidental extrinsic contamination. In another aspect, the formulation, comprises: from 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, to 1.5% w/v of an antimicrobial agent. Additional examples include: from 0.01-0.5% w/v, 0.05% w/v, 0.1% w/v, 0.2% w/v and 0.4% w/v.

In another aspect, the formulation, comprises: from 2, 3, 4, 5, 6, 7, 8, 9, 10, 11, 12, 13, 14, 15, 16, 17, 18, 19, 20, 21, 22, 23, 24, 25, 26, 27, 28, 29, to 30% v/v of a lipid. Additional examples include: from 5-30% w/v, 15-25% v/v and 20% v/v.

In another aspect, the formulation, comprises: from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, to 2% w/v of an emulsifier. Additional examples include: from 0.5-1.5% w/v, 1-2% w/v, and 1.2% w/v.

In another aspect, the formulation, comprises: from 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, to 4% w/v of a tonicity modifier. Additional examples include: 2-3% w/v; 2.1, 2.15, 2.2, 2.25, 2.3, 2.35, to 2.4% w/v; and, 2.25% w/v.

In another aspect, the formulation, comprises: from 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to 5% v/v of a co-emulsifier. Additional examples include: 0.2-3% w/v, 0.5-2% w/v, 0.5% w/v, 1% w/v, 1.5% w/v, and 2% w/v.

In another aspect, the formulation, comprises: from 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, to 1% w/v of an antioxidant. Additional examples include: 0.02-0.5% w/v, and 0.1% w/v.

In another aspect, the formulation, comprises: water to 100%.

In another aspect, the average particle size of the formulation is from 70, 80, 90, 100, 110, 120, 130, 140, 150, 160, 170, to 180 (+/−20 nm) in diameter. Additional examples include (a) 90 nm (+/−20 nm), (b) 110-120 nm (+/−20 nm), and (c) 150-180 nm (+/−20 nm).

In another aspect, the present invention provides a novel metolazone oil-in-water emulsion formulation comprising: one of Examples A-WW in Table A (wherein water is present to 100%):

TABLE A

Metolazone is optionally a pharmaceutically acceptable salt thereof.

| Ex. | Metolazone mg/mL | Lipid % v/v | Emulsifier % w/v | Tonicity modifier % w/v | CoEmulsifier % v/v | Antimicrobial % w/v | Antioxidant % w/v |
|---|---|---|---|---|---|---|---|
| A. | 0.1-5 | 2-30 | 0.1-2 | 1-4 | | | |
| B. | 0.2-2 | 15-25 | 1-2 | 2-3 | | | |
| C. | 0.5-1 | 20 | 1.2 | 2.25 | | | |
| D. | 0.5 | 20 | 1.2 | 2.25 | | | |
| E. | 1 | 20 | 1.2 | 2.25 | | | |
| F. | 0.1-5 | 2-30 | 0.1-2 | 1-4 | 0.05-5 | | |
| G. | 0.2-2 | 15-25 | 1-2 | 2-3 | 0.2-3 | | |
| H. | 0.5-1 | 20 | 1.2 | 2.25 | 0.5-2 | | |
| I. | 0.5 | 20 | 1.2 | 2.25 | 0.5 | | |
| J. | 0.5 | 20 | 1.2 | 2.25 | 1 | | |
| K. | 0.5 | 20 | 1.2 | 2.25 | 1.5 | | |
| L. | 0.5 | 20 | 1.2 | 2.25 | 2 | | |
| M. | 1 | 20 | 1.2 | 2.25 | 0.5 | | |
| N. | 1 | 20 | 1.2 | 2.25 | 1 | | |
| O. | 1 | 20 | 1.2 | 2.25 | 1.5 | | |
| P. | 1 | 20 | 1.2 | 2.25 | 2 | | |
| Q. | 0.1-5 | 2-30 | 0.1-2 | 1-4 | 0.05-5 | 0.001-1 | |
| R. | 0.2-2 | 15-25 | 1-2 | 2-3 | 0.2-3 | 0.01-0.5 | |
| S. | 0.5-1 | 20 | 1.2 | 2.25 | 0.5-2 | 0.05 | |
| T. | 0.5 | 20 | 1.2 | 2.25 | 0.5 | 0.05 | |
| U. | 0.5 | 20 | 1.2 | 2.25 | 1 | 0.05 | |
| V. | 0.5 | 20 | 1.2 | 2.25 | 1.5 | 0.05 | |
| W. | 0.5 | 20 | 1.2 | 2.25 | 2 | 0.05 | |
| X. | 1 | 20 | 1.2 | 2.25 | 0.5 | 0.05 | |
| Y. | 1 | 20 | 1.2 | 2.25 | 1 | 0.05 | |
| Z. | 1 | 20 | 1.2 | 2.25 | 1.5 | 0.05 | |
| AA. | 1 | 20 | 1.2 | 2.25 | 2 | 0.05 | |
| BB. | 0.1-5 | 2-30 | 0.1-2 | 1-4 | 0.05-5 | | 0.01-1 |
| CC. | 0.2-2 | 15-25 | 1-2 | 2-3 | 0.2-3 | | 0.02-0.5 |
| DD. | 0.5-1 | 20 | 1.2 | 2.25 | 0.5-2 | | 0.1 |
| EE. | 0.5 | 20 | 1.2 | 2.25 | 0.5 | | 0.1 |
| FF. | 0.5 | 20 | 1.2 | 2.25 | 1 | | 0.1 |
| GG. | 0.5 | 20 | 1.2 | 2.25 | 1.5 | | 0.1 |
| HH. | 0.5 | 20 | 1.2 | 2.25 | 2 | | 0.1 |
| II. | 1 | 20 | 1.2 | 2.25 | 0.5 | | 0.1 |
| JJ. | 1 | 20 | 1.2 | 2.25 | 1 | | 0.1 |
| KK. | 1 | 20 | 1.2 | 2.25 | 1.5 | | 0.1 |
| LL. | 1 | 20 | 1.2 | 2.25 | 2 | | 0.1 |

TABLE A-continued

Metolazone is optionally a pharmaceutically acceptable salt thereof.

| Ex. | Metolazone mg/mL | Lipid % v/v | Emulsifier % w/v | Tonicity modifier % w/v | CoEmulsifier % v/v | Antimicrobial % w/v | Antioxidant % w/v |
|---|---|---|---|---|---|---|---|
| MM. | 0.1-5 | 2-30 | 0.1-2 | 1-4 | 0.05-5 | 0.001-1 | 0.01-1 |
| NN. | 0.2-2 | 15-25 | 1-2 | 2-3 | 0.2-3 | 0.01-0.5 | 0.02-0.5 |
| OO. | 0.5-1 | 20 | 1.2 | 2.25 | 0.5-2 | 0.05 | 0.1 |
| PP. | 0.5 | 20 | 1.2 | 2.25 | 0.5 | 0.05 | 0.1 |
| QQ. | 0.5 | 20 | 1.2 | 2.25 | 1 | 0.05 | 0.1 |
| RR. | 0.5 | 20 | 1.2 | 2.25 | 1.5 | 0.05 | 0.1 |
| SS. | 0.5 | 20 | 1.2 | 2.25 | 2 | 0.05 | 0.1 |
| TT. | 1 | 20 | 1.2 | 2.25 | 0.5 | 0.05 | 0.1 |
| UU. | 1 | 20 | 1.2 | 2.25 | 1 | 0.05 | 0.1 |
| VV. | 1 | 20 | 1.2 | 2.25 | 1.5 | 0.05 | 0.1 |
| WW. | 1 | 20 | 1.2 | 2.25 | 2 | 0.05 | 0.1 |

In another aspect, the present invention provides a novel metolazone oil-in-water emulsion formulation comprising: one of Examples A-WW in Table B (wherein water is present to 100%):

TABLE B

Metolazone is optionally a pharmaceutically acceptable salt thereof.

| Ex. | Metolazone mg/mL | Soybean Oil % v/v | L-α-Lecithin soybean % w/v | Glycerin % w/v | Polysorbate 80 % v/v | EDTA % w/v | Sodium Ascorbate % w/v |
|---|---|---|---|---|---|---|---|
| 1. | 0.1-5 | 2-30 | 0.1-2 | 1-4 | | | |
| 2. | 0.2-2 | 15-25 | 1-2 | 2-3 | | | |
| 3. | 0.5-1 | 20 | 1.2 | 2.25 | | | |
| 4. | 0.5 | 20 | 1.2 | 2.25 | | | |
| 5. | 1 | 20 | 1.2 | 2.25 | | | |
| 6. | 0.1-5 | 2-30 | 0.1-2 | 1-4 | 0.05-5 | | |
| 7. | 0.2-2 | 15-25 | 1-2 | 2-3 | 0.2-3 | | |
| 8. | 0.5-1 | 20 | 1.2 | 2.25 | 0.5-2 | | |
| 9. | 0.5 | 20 | 1.2 | 2.25 | 0.5 | | |
| 10. | 0.5 | 20 | 1.2 | 2.25 | 1 | | |
| 11. | 0.5 | 20 | 1.2 | 2.25 | 1.5 | | |
| 12. | 0.5 | 20 | 1.2 | 2.25 | 2 | | |
| 13. | 1 | 20 | 1.2 | 2.25 | 0.5 | | |
| 14. | 1 | 20 | 1.2 | 2.25 | 1 | | |
| 15. | 1 | 20 | 1.2 | 2.25 | 1.5 | | |
| 16. | 1 | 20 | 1.2 | 2.25 | 2 | | |
| 17. | 0.1-5 | 2-30 | 0.1-2 | 1-4 | 0.05-5 | 0.001-1 | |
| 18. | 0.2-2 | 15-25 | 1-2 | 2-3 | 0.2-3 | 0.01-0.5 | |
| 19. | 0.5-1 | 20 | 1.2 | 2.25 | 0.5-2 | 0.05 | |
| 20. | 0.5 | 20 | 1.2 | 2.25 | 0.5 | 0.05 | |
| 21. | 0.5 | 20 | 1.2 | 2.25 | 1 | 0.05 | |
| 22. | 0.5 | 20 | 1.2 | 2.25 | 1.5 | 0.05 | |
| 23. | 0.5 | 20 | 1.2 | 2.25 | 2 | 0.05 | |
| 24. | 1 | 20 | 1.2 | 2.25 | 0.5 | 0.05 | |
| 25. | 1 | 20 | 1.2 | 2.25 | 1 | 0.05 | |
| 26. | 1 | 20 | 1.2 | 2.25 | 1.5 | 0.05 | |
| 27. | 1 | 20 | 1.2 | 2.25 | 2 | 0.05 | |
| 28. | 0.1-5 | 2-30 | 0.1-2 | 1-4 | 0.05-5 | | 0.01-1 |
| 29. | 0.2-2 | 15-25 | 1-2 | 2-3 | 0.2-3 | | 0.02-0.5 |
| 30. | 0.5-1 | 20 | 1.2 | 2.25 | 0.5-2 | | 0.1 |
| 31. | 0.5 | 20 | 1.2 | 2.25 | 0.5 | | 0.1 |
| 32. | 0.5 | 20 | 1.2 | 2.25 | 1 | | 0.1 |
| 33. | 0.5 | 20 | 1.2 | 2.25 | 1.5 | | 0.1 |
| 34. | 0.5 | 20 | 1.2 | 2.25 | 2 | | 0.1 |
| 35. | 1 | 20 | 1.2 | 2.25 | 0.5 | | 0.1 |
| 36. | 1 | 20 | 1.2 | 2.25 | 1 | | 0.1 |
| 37. | 1 | 20 | 1.2 | 2.25 | 1.5 | | 0.1 |
| 38. | 1 | 20 | 1.2 | 2.25 | 2 | | 0.1 |
| 39. | 0.1-5 | 2-30 | 0.1-2 | 1-4 | 0.05-5 | 0.001-1 | 0.01-1 |
| 40. | 0.2-2 | 15-25 | 1-2 | 2-3 | 0.2-3 | 0.01-0.5 | 0.02-0.5 |
| 41. | 0.5-1 | 20 | 1.2 | 2.25 | 0.5-2 | 0.05 | 0.1 |
| 42. | 0.5 | 20 | 1.2 | 2.25 | 0.5 | 0.05 | 0.1 |
| 43. | 0.5 | 20 | 1.2 | 2.25 | 1 | 0.05 | 0.1 |
| 44. | 0.5 | 20 | 1.2 | 2.25 | 1.5 | 0.05 | 0.1 |
| 45. | 0.5 | 20 | 1.2 | 2.25 | 2 | 0.05 | 0.1 |
| 46. | 1 | 20 | 1.2 | 2.25 | 0.5 | 0.05 | 0.1 |

TABLE B-continued

Metolazone is optionally a pharmaceutically acceptable salt thereof.

| Ex. | Metolazone mg/mL | Soybean Oil % v/v | L-α-Lecithin soybean % w/v | Glycerin % w/v | Polysorbate 80 % v/v | EDTA % w/v | Sodium Ascorbate % w/v |
|---|---|---|---|---|---|---|---|
| 47. | 1 | 20 | 1.2 | 2.25 | 1 | 0.05 | 0.1 |
| 48. | 1 | 20 | 1.2 | 2.25 | 1.5 | 0.05 | 0.1 |
| 49. | 1 | 20 | 1.2 | 2.25 | 2 | 0.05 | 0.1 |

In another aspect, the formulation is passed one or more times through a high-pressure homogenizer to reduce particle size.

In another aspect, the formulation is passed through a microfluidics system one or more times to reduce particle size and/or to enhance stability.

In another aspect, the formulation undergoes ultra-high-pressure homogenization as well as through a microfluidics system.

In another aspect, the formulation the lipid emulsion is processed using a high-pressure homogenizer and/or a microfluidics system that obviates the need for a co-emulsifier e.g.: Tween 80 or poloxamer 188.

In another aspect, the formulation is sterile.

In another aspect, in the event of accidental contamination, the pharmaceutical formulation will retard the growth of microorganisms to no more than 1 log within at least 24 hours.

In another aspect, metolazone and the emulsion maintain their stability in the formulation. In another aspect, the emulsion is stable for 1, 2, 3, 4, 5, 6, 7, 8, 9, 10, 11, to 12 months at room temperature. A stable formulation is expected to appear homogeneous (e.g., having an equal distribution of metolazone and other formulation components). In contrast, an unstable formulation (or one that has lost its stability) is one that shows layers, clumping, precipitation, or on some away appears non-homogeneous.

In another aspect, the formulation is for parenteral administration.

In another aspect, the pH of the formulation ranges from 6.0, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, to 8.8. In another aspect, the pH ranges from 7-8. In another aspect, the pH ranges from 7.6-7.8. Bases such as NaOH, KOH, and Ca(OH)$_2$ may be used to achieve a desired pH. Alternatively, an acid (e.g., HCl), if need, may be used to achieve a desired pH.

"Metolazone" includes all varieties or forms of metolazone. Unless otherwise specified, examples of such forms include pharmaceutically acceptable salts, and crystalline and amorphous forms.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Antimicrobial agent" means an agent that inhibits the growth of microorganisms such as bacteria and fungi (molds and yeast). Examples of classes of antimicrobial agents include chelating agents and alcohols. Chelating agents include, but are not limited to, ethylenediamine tetraacetic acid (EDTA) and salts thereof, citric acid and salts thereof, and the like. Alcohols include, but are not limited to, benzyl alcohol and chlorobutanol. Examples of antimicrobial agents include EDTA, ascorbic acid, BHA/BHT, benzyl alcohol, benzoic acid, citric acid, edetic acid, parabens, phenol, propyl gallate, sorbic acid, sodium bisulfite, sodium sulfite, benzoic acid, chlorobutanol, chlorocresol, cresol, dehydroacetic acid, phenol, potassium benzoate, potassium sorbate, sodium benzoate, sodium dehydroacetate, sodium propionate, sorbic acid, thymol, benzalkonium chloride, benzethonium chloride, butyl paraben, cetylpyridinium chloride, ethylparaben, methylparaben, methylparaben sodium, propylparaben, propylparaben sodium, chlorocresol, cresol, dehydroacetic acid, ethylparaben, methylparaben, methylparaben sodium, phenol, potassium sorbate, thimersol and the various salt forms for these compounds.

In another aspect, the antimicrobial agent is an alcohol or a chelating agent. In another aspect, the antimicrobial agent is selected from: disodium edetate (EDTA), sodium citrate, and a combination of both. In another aspect, the antimicrobial is EDTA. In another aspect, the antimicrobial is a combination of EDTA and sodium citrate.

In another aspect, the antimicrobial agent may comprise more than one agent, including two, three, or four different antimicrobial agents.

"Antioxidant" means an agent that will slow or inhibit oxidation of components of the formulation. Examples include sodium ascorbate, cysteine hydrochloride, sodium bisulfite, sodium metabisulfite, sodium sulfite, ascorbyl palmitate, butylated hydroxyanisole (BHA), butylated hydroxytoluene (BHT), propyl gallate, tocopherol, and their pharmaceutically acceptable salts.

In another aspect, the antioxidant is sodium ascorbate.

"Lipid" means any pharmaceutically acceptable oil, including a triglyceride such as soybean oil, safflower seed oil, olive oil, cottonseed oil, sunflower oil, sesame oil, peanut oil, corn oil, a medium chain triglyceride (such as Miglyol™ 812 or 810) or triacetin. The lipid may also be a propylene glycol diester or monoglyceride (such as acetylareal monoglyceride). The lipid can also be a mixture of one or more lipids.

In another aspect, the lipid is soybean oil.

"Emulsifier" refers to a suitable pharmaceutically acceptable surfactant. Examples include naturally occurring phospholipids extracted from egg yolk or soybean (e.g., L-α-lecithin, soybean (or other sources)), synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soya).

"Co-emulsifier" refers to a second pharmaceutically acceptable surfactant that may be included in the formulations of the invention. Such surfactants include synthetic nonionic surfactants such as poloxamers (for example Poloxamer 188 and 407), cremophor, poloxamines, polyoxyethylene stearates, polyoxyethylene sorbitan fatty acid esters or sorbitan fatty acid esters (e.g., polysorbates 20, 40, 60, and 80), derivatives of tocopherol such as tocopherol PEG succinate, long chain fatty acids such as oleic acid, stearic acid, palmitic acid, bile acids such as cholic acid and deoxycholic acid or surface active derivatives, and pharmaceutically acceptable salts thereof.

In another aspect, the co-emulsifier is polysorbate 80.

In another aspect, the co-emulsifier is oleic acid.

"Tonicity modifier" refers to agents including sodium chloride, sodium acetate, potassium chloride, mannitol, sucrose, lactose, fructose, maltose, dextrose, dextrose anhydrous, propylene glycol, glycerol, and glycerin. The terms "tonicity modifier" and "isotonicity adjuster" are used herein interchangeably.

In another aspect, the tonicity modifier is glycerin.

The amount of water in the formulations of the present invention, such as water-for-injections, is used to make up the volume to 100% w/v and can vary depending on the total overall volume of the formulation and the concentration of the other components.

As the formulations of the present invention are intended for parenteral administration, the skilled artisan will understand that one or more additional components used in parenteral formulations may be included. Such additional components include stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG), buffers (e.g. acetates, citrates, phosphates, tartrates, lactates, succinates, amino acids and the like), preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), suspending or viscosity agents, chelating agents, and administration aids (e.g. local anesthetics, anti-inflammatory agents, anti-clotting agents, vasoconstrictors for prolongation and agents that increase tissue permeability).

Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intraarticular (joint), intrasynovial (joint fluid area), intracranial, intraspinal, and intrathecal (spinal fluids). Any known device useful for parenteral injection or infusion of drug formulations can be used to effect such administration.

In intravenous use, a sterile formulation of the present invention can be dissolved or suspended in any of the commonly used sterile intravenous fluids and administered by infusion. Intravenous fluids include, without limitation, physiological saline, phosphate buffered saline, 5% dextrose in water or Ringer's solution. The parenteral dosage form of formulations of the present invention can also be a ready-to-use solution in sterile sealed vials, hermetically sealed ampoules or in sterile pre-filled syringes, for example.

Sterile pre-filled syringes are syringes that contain a unit dose of a formulation of the present invention. Suitable syringes are widely available and well known to the skilled artisan. In an aspect, a sterile pre-filled syringe is one that has been loaded with a unit dose of the pharmaceutical formulation and that is enclosed in an opaque, sealed package from which oxygen has been excluded. For example, oxygen may be displaced with $CO_2$ and/or $N_2$.

In an aspect, a pre-filled syringe contains from 0.5, 0.6, 0.7, 0.8, 0.9, 1, 2, 3, 4, 5, 6, 7, 8, 9, to 10 mg of metolazone. In another aspect, a container other than a pre-filled syringe may be used (e.g., vial, IV bag, etc.). In another aspect, a multi-use container (e.g., vial or IV bag) contains from 5, 10, 15, 20, 25, 30, 35, 40, 45, 50, 55, 60, 65, 70, 75, 80, 85, 90, 90, to 100 mg of metolazone.

The terms "inhibit", "inhibiting" and "inhibition" have their ordinary and customary meanings, and include inhibiting the growth of a bacteria or fungus in the formulations of the present invention. Such inhibition may be described as no more than about 10 fold growth for at least 24 hours following a low level (1-1000 Cfu/mL) of extrinsic contamination. Such growth may be determined, for example, by determining the number of colony forming units in the formulation when cultured at room temperature.

The duration of time over which inhibition of microbial growth is maintained will vary depending on the environmental conditions to which the formulation is exposed, e.g., the conditions under which a sterile vial of the formulation is pierced by a needle or sterility is otherwise breached. However, in an aspect of the invention, microbial growth is inhibited for at least about 24 or more hours after the formulation is exposed to low level extrinsic microbial contamination.

Other features of the invention will become apparent in the course of the following descriptions of exemplary embodiments that are given for illustration of the invention and are not intended to be limiting thereof.

EXAMPLES

The skilled artisan will understand that the pharmaceutical formulations of the present invention may be prepared using art-accepted means for preparing emulsion formulations.

A general procedure for preparing metolazone formulations is described as follows: an oil phase containing soybean oil, metolazone, and L-α-lecithin, soybean is mixed with an aqueous phase containing glycerin, at approximately 70° C. to form a coarse emulsion. The pH of the coarse emulsion can be adjusted using NaOH or HCl as needed.

Following pH adjustment, the coarse emulsion is homogenized under high pressure to produce a fine particle size and thus a stable emulsion. The emulsion is filled into appropriate containers and optionally sterilized in an autoclave.

An alternative general procedure is as follows: metolazone and L-α-lecithin were dissolved in soybean oil with gentle heating and stirring to form an oil phase. Glycerin and polysorbate 80 were added to water. The oil phase was slowly added to the water phase with vigorous stirring. On completion of addition of the oil phase, the mixture was homogenized for an additional 3 minutes to form an emulsion. The emulsion is filled into appropriate containers and can be sterilized in an autoclave or sterilized by in-process filtration employing a Millipore filter, 0.22 μm, or using multiple filters in series.

Examples 1-24 shown below are representative 20 mL formulations of the present invention. Water is not shown but is present to make a final volume of 20 mL.

TABLE 1

The average hydrodynamic diameter (z-average ± standard deviation) of a blank lipid emulsion, which contains no metolazone, with various concentrations of tween 80.

| Formulation | Particle Size (nm) | Sample Age |
|---|---|---|
| 0.5% Tween 80 | 834.2 ± 36.3 | 24 hrs |
| 2% Tween 80 | 364.5 ± 15.12 | 24 hrs |
| 5% Tween 80 | 283.03 ± 16.84 | 24 hrs |
| 5% Tween 80% | 259.87 ± 3.7 | 4 weeks |

Samples were stored at 4° C. (N = 3)

| Ex. | Metolazone | Soybean Oil | L-α-Lecithin soybean | Glycerin | Polysorbate 80 | EDTA | Sodium Ascorbate |
|---|---|---|---|---|---|---|---|
| 1. | 10 mg | 4 mL | 240 mg | 450 mg | 0.1 mL | | |
| 2. | 10 mg | 4 mL | 240 mg | 450 mg | 0.2 mL | | |
| 3. | 10 mg | 4 mL | 240 mg | 450 mg | 0.4 mL | | |
| 4. | 20 mg | 4 mL | 240 mg | 450 mg | 0.1 mL | | |
| 5. | 20 mg | 4 mL | 240 mg | 450 mg | 0.2 mL | | |
| 6. | 20 mg | 4 mL | 240 mg | 450 mg | 0.4 mL | | |
| 7. | 10 mg | 4 mL | 240 mg | 450 mg | 0.1 mL | 1 mg | |
| 8. | 10 mg | 4 mL | 240 mg | 450 mg | 0.2 mL | 1 mg | |
| 9. | 10 mg | 4 mL | 240 mg | 450 mg | 0.4 mL | 1 mg | |
| 10. | 20 mg | 4 mL | 240 mg | 450 mg | 0.1 mL | 1 mg | |
| 11. | 20 mg | 4 mL | 240 mg | 450 mg | 0.2 mL | 1 mg | |
| 12. | 20 mg | 4 mL | 240 mg | 450 mg | 0.4 mL | 1 mg | |
| 13. | 10 mg | 4 mL | 240 mg | 450 mg | 0.1 mL | | 20 mg |
| 14. | 10 mg | 4 mL | 240 mg | 450 mg | 0.2 mL | | 20 mg |
| 15. | 10 mg | 4 mL | 240 mg | 450 mg | 0.4 mL | | 20 mg |
| 16. | 20 mg | 4 mL | 240 mg | 450 mg | 0.1 mL | | 20 mg |
| 17. | 20 mg | 4 mL | 240 mg | 450 mg | 0.2 mL | | 20 mg |
| 18. | 20 mg | 4 mL | 240 mg | 450 mg | 0.4 mL | | 20 mg |
| 19. | 10 mg | 4 mL | 240 mg | 450 mg | 0.1 mL | 1 mg | 20 mg |
| 20. | 10 mg | 4 mL | 240 mg | 450 mg | 0.2 mL | 1 mg | 20 mg |
| 21. | 10 mg | 4 mL | 240 mg | 450 mg | 0.4 mL | 1 mg | 20 mg |
| 22. | 20 mg | 4 mL | 240 mg | 450 mg | 0.1 mL | 1 mg | 20 mg |
| 23. | 20 mg | 4 mL | 240 mg | 450 mg | 0.2 mL | 1 mg | 20 mg |
| 24. | 20 mg | 4 mL | 240 mg | 450 mg | 0.4 mL | 1 mg | 20 mg |

Example 25

A formulation of the present invention was made as follows.

1) 600 mg of L-α-Lecithin soybean was dissolved in 5 mL soybean oil.
2) 50 mg Metolazone was added to this oil mixture.
3) An additional 5 mL soybean oil was then added to the oil mixture.
4) 1 mL polysorbate 80 and 364 μL glycerin were added to 14.6 mL water to form the water phase.
5) 4 mL of the oil phase was added to the water phase.

The average hydrolysis diameter of a blank lipid emulsion was as seen in Table 1 without metolazone.

When metolazone was added, the results are seen in Table 2.

TABLE 2

The average hydrodynamic diameter (z-average ± standard deviation) of lipid emulsion, containing 1 mg/ml metolazone, with various concentrations of Tween 80.

| Formulation | Particle Size (nm) | Sample Age |
|---|---|---|
| 0% Tween 80 | Separated out | |
| 0.25% Tween 80 | Separated out | |
| 0.5% Tween 80 | 713.83 ± 57.09 | 24 hrs |
| 0.5% Tween 80 | 929.4 ± 102.71 | 24 hrs |
| 2% Tween 80 | 307.83 ± 29.13 | 24 hrs |
| 5% Tween 80 | 261.17 ± 10.82 | 24 hrs |
| 5% Tween 80 | 259.62 ± 12.43 | 7 days |

TABLE 2-continued

The average hydrodynamic diameter (z-average ± standard deviation) of lipid emulsion, containing 1 mg/ml metolazone, with various concentrations of Tween 80.

| Formulation | Particle Size (nm) | Sample Age |
|---|---|---|
| 5% Tween 80 | 296.5 ± 7.45 | 2 weeks |
| 5% Tween 80 | 266.13 ± 14.75 | 3 weeks |
| 5% Tween 80 | 248.73 ± 51.09 | 12 weeks |

The results reveal that adding metolazone to the emulsion does not appear to significantly alter particle size when the Tween emulsifier is employed. The emulsion containing 5% Tween 80 showed a more consistent particle size distribution with each run and was visually more stable as compared to the emulsion containing 2% Tween 80.

The stability of the material at different pH's was further evaluated (Table 3). The material was found to be stable at a wide range of pH's.

TABLE 3

The average hydrodynamic diameter (z-average ± standard deviation) of lipid emulsion, 5% Tween 80 and 1 mg/ml metolazone at various pH's.

| Formulation | Particle Size (nm) | Zeta Potential (mV) | Sample Age |
|---|---|---|---|
| 5.5 | 284.1 ± 22.7 | −7.19 ± 0.33 | <24 hrs |
| 6.0 | 313.2 ± 9.1 | −19.9 ± 0.87 | <24 hrs |
| 7.0 | 215.6 ± 7.9 | −14.23 ± 0.5 | <24 hrs |
| 8.48 | 294.9 ± 25 | −26.37 ± 0.47 | <24 hrs |

Additionally, the metolazone in 5% Tween 80 appears to be stable with consistent preservation of particle size (Table 4).

TABLE 4

The average particle size of a lipid emulsion containing 5% Tween 80 and 1 mg/ml metolazone dispersed in D5W (Dextrose 5% water) or normal saline (0.9% sodium chloride) (N = 3).

| Formulation is in: | Particle Size (nm) |
|---|---|
| D5W | 304.8 ± 8.7 |
| 0.9% Sodium Chloride | 271.1 ± 27.8 |

To further reduce particle size the emulsion was subjected to high pressure homogenization at 5,000 psi for 5 cycles (Table 5). The emulsion was dispersed in 10 mM NaCl.

TABLE 5

The average particle size of a lipid emulsion containing 5% Tween 80 and 1 mg/ml metolazone.

| Particle Size (nm) | PDI | Zeta Potential (mV) |
|---|---|---|
| 157.13 ± 1.52 | 0.182 ± 0.015 | −4.53 ± 0.19 |

The results show that the emulsion has a Polydispersity Index (PDI) less than 0.2, which means the emulsion is homogenously sized.

We further evaluated a lipid emulsion containing 1% Tween 80 and 1 mg/mL metolazone. The emulsion subjected to high pressure homogenization with various pressures for 10 cycles. (see Table 6). The emulsion was dispersed in 10 mM NaCl.

TABLE 6

The average particle size of a lipid emulsion containing 1% Tween 80 and 1 mg/ml metolazone.

| Pressure | Particle Size (nm) | PDI |
|---|---|---|
| 5,000 | 167.13 ± 2.57 | 0.07 ± 0.03 |
| 10,000 | 155.46 ± 0.63 | 0.19 ± 0.25 |
| 20,000 | 148.01 ± 6.03 | 0.086 ± 0.02 |
| 27,000 | 160.33 ± 0.45 | 0.091 ± 0.029 |

Using a lower concentration of the emulsifier still results in a Polydispersity Index of less than 0.2, suggesting a homogenously sized emulsion. The emulsion was also stable using the reduced emulsifier concentration. There was no significant difference in particle size or polydispersity where the emulsion was subjected to 20,000 or 27,000 psi.

Example 26

A formulation of the present invention was using a second alternative surfactant was utilized, poloxamer 188. The formulation contained:
12 mg/mL, L-α-Lecithin soybean
20% v/v Soybean oil
2.25% w/v Glycerin
3% w/v Poloxamer 188
1 mg/mL Metolazone
Water: qs
Final emulsion volume 20 mL The formulation of Example 26 was formulated as follows.
1) L-α-Lecithin was dissolved in half of the amount of soybean oil at 70° C., 200 rpm for 2 hours.
2) Metolazone was added with gentle heating and stirring for an additional hour.
3) The remaining amount of soybean oil was added.
4) The water phase was prepared by adding 2.25% w/v glycerin and 3% w/v poloxamer 188 to water with gently mixing.
5) The oil phase was slowly added to the water phase with vigorous mixing. On completing the addition of the oil phase, the mixture was subjected to high pressure homogenization for an additional 5 minutes.

The resulting emulsion was stable and found to have characteristics as described in Table 1 below:

TABLE 1

The average hydrodynamic diameter (z-average ± standard deviation) of a 1 mg/ml metolazone lipid emulsion with various concentrations of poloxamer 188.

| Formulation | Particle Size (nm) |
|---|---|
| With 1% Poloxamer 188 | 382.9 ± 31.4 |
| With 3% Poloxamer 188 | 299.97 ± 14.89 |
| With 5% Poloxamer 188 | 760.67 ± 168.2 |
| With 1% Poloxamer 188 | 273.1 ± 23.2 |
| With 3% Poloxamer 188 | 295.07 ± 14.76 |

The emulsion was dispersed in 20 ml of 10 nM NaCl. The 3% poloxamer 188 produced a uniform, homogenetic particle size distribution that was stable at RT.

Example 27

Studies were performed employing a microfluidics process on the Lecithin soybean oil and glycerin formulation with Tween that resulted in a stable formulation with a particle size ranging from 72.8 nm-101 nm with excellent homogeneity (polydispersity index). Using the microfluidics system without the second emulsifier (Tween 80) resulted in a similar particle size. High pressure homogenization did not further reduce particle size. The microfluidizer used was the F12Y-H30Z interaction chamber configuration and at 20,000 psi. The particle size was as shown below in Table 1.

TABLE 1

The average hydrodynamic diameter (z-average ± standard deviation) of a 1 mg/ml metolazone lipid emulsion with various concentrations of poloxamer 188.

| # of passes | Z average | PdI | d10 (nm) | d50 (nm) | d90 (nm) |
|---|---|---|---|---|---|
| 1 | 149.8 | 0.093 | 101 | 157 | 247 |
| 3 | 128.9 | 0.117 | 84.5 | 134 | 219 |
| 5 | 118.2 | 0.108 | 77.9 | 124 | 207 |
| 7 | 115.4 | 0.074 | 79.9 | 121 | 184 |
| 10 | 109.9 | 0.085 | 72.8 | 116 | 184 |

Based on the above studies, metolazone can be placed in a stable lipid emulsion. Adding additional emulsifiers (Tween for example) aids in stability and with high pressure homogenization reduces particle size within the range requisite for in-process sterilization. Furthermore, the work incorporating microfluidics shows that the formulation may not require a second emulsifier, e.g. Tween 80, or high pressure homogenization. The microfluidics approach will reduce particle size to the extent required for a stable formulation that can be filtered through a Millipore filter for in-process sterilization.

Example 28

The utility of the IV metolazone lipid emulsion formulation is dependent on its biologic action. We evaluated the formulation with Tween 80 in 12 Sprague-Dawley male rats (400-500 g). After a 48 hr acclimation period, 24 hr baseline urine collection was undertaken employing a metabolic cage. Then IP injections were administered at 2 mg/kg (6 rats) and 4 mg/kg (6 rats). The effect of two doses of methadone are shown in FIG. 1.

Urine volume and electrolytes were then determined for baseline and following IP diuretic administration. All animals had free access to water. Twenty-four-hour baseline urine volume was 13.5±3 ml, which increased to 22.8±3.5 ml after 2 mg dose (p<0.01) and 31±5 ml after 4 mg dose (p<0.05). Urine volume showed an increase of 69% after 2 mg and a 129% increase over baseline after 4 mg IV metolazone. Urine $Na^+$ concentration increased from 1.33±0.45 mEq at baseline to 2.58±0.42 (94% increase); urine $K^+$ 0.12±0.48 mEq to 0.76±0.39 (533% increase) and Cl 1.47±0.62 mEq to 3.31±0.75 (125% increase); p<0.01 at 2 mg/kg IP dose. At the 4 mg/kg dose, urine $Na^+$ increased from 1.6±4 to 4.3±0.2 mEq (168%); urine $K^+$ increased from 3.1±0.03 to 3.9±0.3 mEq (26%) and Cl 2.2±0.3 to 5.52±0.13 (151%).

The results confirm the potent natriuretic and diuretic properties of metolazone and demonstrate the biologic activity of the present lipid formulation.

Numerous modifications and variations of the present invention are possible in light of the above teachings. It is therefore to be understood that within the scope of the appended claims, the invention may be practiced otherwise that as specifically described herein.

What is claimed is:

1. An intravenous metolazone oil-in-water emulsion formulation, comprising:
   a) 0.1-10 mg/mL of metolazone or a pharmaceutically acceptable salt thereof;
   b) 2-30% v/v of a lipid selected from the group consisting of soybean oil, safflower seed oil, olive oil, cottonseed oil, sunflower oil, sesame oil, peanut oil, corn oil, medium chain triglycerides, triacetin, propylene glycol diesters, monoglycerides, and a mixture of two or more thereof;
   c) 0.1-2% w/v of an emulsifier selected from the group consisting of egg yolk phospholipids, soybean phospholipids, synthetic phosphatidyl cholines, purified phosphatidyl cholines and hydrogenated phosphatidyl choline, and mixtures of two or more thereof;
   d) water;
   e) 1-4% w/v of a tonicity modifier selected from the group consisting of sodium chloride, sodium acetate, potassium chloride, mannitol, sucrose, lactose, fructose, maltose, dextrose, dextrose anhydrous, and glycerin; and,
   f) 0.05-5% v/v of a co-emulsifier selected from the group consisting of poloxamers, polyoxyethylene stearates, sorbitan fatty acid esters, polysorbates, tocopherol PEG succinate, cholic acid, deoxycholic acid, oleic acid, and pharmaceutically acceptable salts thereof;
   wherein the formulation is suitable for intravenous administration; and
   wherein benzyl alcohol is excluded.

2. The formulation of claim 1, further comprising:
   g) 0.001-1% w/v of an antimicrobial agent.

3. The formulation of claim 2, wherein the antimicrobial agent is selected from the group consisting of EDTA, sodium ascorbate, citric acid, and mixtures and salts thereof.

4. The formulation of claim 2, wherein the antimicrobial agent is EDTA.

5. The formulation of claim 1, wherein the formulation has a pH of 6.0-8.8.

6. The formulation of claim 1, wherein the lipid is soybean oil.

7. The formulation of claim 1, wherein the emulsifier is L-α-Lecithin.

8. The formulation of claim 1, wherein the co-emulsifier is polysorbate 80.

9. The formulation of claim 1, wherein the co-emulsifier is poloxamer 188.

10. The formulation of claim 1, wherein the tonicity agent is glycerin.

11. The formulation of claim 1, further comprising:
    h) an antioxidant, present at about 0.01 to about 1.0% w/v.

12. The formulation of claim 11, wherein the antioxidant is selected from the group consisting of sodium ascorbate, sodium citrate, cysteine hydrochloride, sodium bisulfate, sodium metabisulfite, sodium sulfite, ascorbyl palmitate, butylated hydroxyanisole (BHA), butylated hydroxytoluene (BHT), propyl gallate, tocopherol, and a pharmaceutically acceptable salt thereof.

13. The formulation of claim 11, wherein the antioxidant is sodium ascorbate.

14. The formulation of claim 1, wherein the formulation is contained in a sterile pre-filled syringe.

15. The formulation of claim 1, wherein the formulation, comprises:
    a) 0.1-10 mg/mL of metolazone or a pharmaceutically acceptable salt thereof;
    b) 2-30% v/v of soybean oil;

c) 0.1-2% w/v of L-α-Lecithin;
d) water;
e) 1-4% w/v of glycerin;
0.05-5% v/v of a co-emulsifier selected from the group consisting of poloxamer 188 and polysorbate 80;
wherein the formulation is suitable for intravenous administration.

16. The formulation of claim 15, wherein the co-emulsifier is poloxamer 188.

17. The formulation of claim 15, wherein the co-emulsifier is polysorbate 80.

18. The formulation of claim 1, further comprising:
g) 0.001-1% w/v of an antimicrobial agent.

19. The formulation of claim 18, wherein the antimicrobial agent is selected from the group consisting of EDTA, sodium ascorbate, citric acid, and mixtures and salts thereof.

* * * * *

UNITED STATES PATENT AND TRADEMARK OFFICE
CERTIFICATE OF CORRECTION

| | | |
|---|---|---|
| PATENT NO. | : 11,389,451 B2 | Page 1 of 1 |
| APPLICATION NO. | : 16/640964 | |
| DATED | : July 19, 2022 | |
| INVENTOR(S) | : John Somberg | |

It is certified that error appears in the above-identified patent and that said Letters Patent is hereby corrected as shown below:

On the Title Page

In item (12), replace "John" with "Somberg"

In item (72), replace "Somberg John" with "John Somberg"

Signed and Sealed this
Third Day of June, 2025

Coke Morgan Stewart
*Acting Director of the United States Patent and Trademark Office*